US006399599B1

(12) United States Patent
Albert et al.

(10) Patent No.: US 6,399,599 B1
(45) Date of Patent: Jun. 4, 2002

(54) SUBSTITUTED 2-OXO-1,4-DIAZACYCLOALKANES

(75) Inventors: Rainer Albert, Basel (CH); Josef G. Meingassner, Perchtoldsdorf (AT); Sompong Wattanasin, Hopatcong, NJ (US); Gabriele Weitz-Schmidt, Bad-Krozingen (DE); Karl Welzenbach, Basel (CH); Ulrich Hommel, Mullheim; Claus Ehrhardt, Lorrach, both of (DE); Didier Roche, Lyons (FR); Joerg Kallen, Basel (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/686,511

(22) Filed: Oct. 11, 2000

Related U.S. Application Data

(60) Provisional application No. 60/266,325, filed on Oct. 13, 1999.

(51) Int. Cl.$^7$ .................... C07D 401/06; C07D 243/08; A61K 31/4709; A61K 31/551
(52) U.S. Cl. ...................... 514/218; 540/492
(58) Field of Search ............. 540/492; 514/218

(56) References Cited

U.S. PATENT DOCUMENTS 6,211,183 B1 * 4/2001 Marlowe et al. ....... 514/255.02

FOREIGN PATENT DOCUMENTS

| EP | 365 992 A1 | 5/1990 |
|----|------------|--------|
| EP | 519 433 A1 | 12/1992 |
| WO | WO 96/31214 | 10/1996 |
| WO | WO 99/20618 | 4/1999 |

OTHER PUBLICATIONS

Lammek B. et al., Journal of Peptide Research, vol. 51, No. 2, pp. 149–154 (1998).
Yameshita T. et al., Chem.Pharm.Bull., vol. 45, No. 12, pp. 1940–1944 (1997).
Piercey M. et al., Brain Research, vol. 385, No. 1, pp. 74–85 (1986).
Slides from 18th Annual Meeting of the American Society of Transplantation, May 15–19, 1999.
Slides from Novartis R&D Day—Investor Conference, New York, Sep. 21, 1999.

* cited by examiner

Primary Examiner—Bruck Kifle
(74) Attorney, Agent, or Firm—Norbert Gruenfeld

(57) ABSTRACT

Compounds of formula I

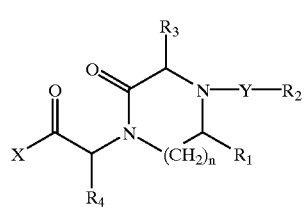

wherein n is 1, 2 or 3; $R_1$ is H, $C_{1-4}$alkyl, aryl, or aryl-$C_{1-4}$alkyl; Y is $C_{1-4}$alkylene, —CO—$C_{1-4}$alkylene, —CO—$C_{2-5}$alkenylene, —CO—NH—, —CO—$C_{1-3}$alkylene-NH—, or —CO—O—; $R_2$ is an aromatic or heteroaromatic residue, each being optionally substituted by $CF_3$, halogen, OH, $C_{1-4}$alkoxy, amino, mono- or di-$C_{1-4}$alkyl substituted amino, phenyl, benzyl or $C_{1-4}$alkyl optionally substituted by amino; $R_3$ is the side chain present on the Cα of an α-amino acid; $R_4$ is biphenylyl, benzyl, hydroxy-benzyl, α- or β-naphthyl-methyl, 5,6,7,8-tetrahydro-β-naphthyl-methyl or indolyl-methyl, each being optionally substituted on the ring by $CF_3$, halogen, OH, $C_{1-4}$alkoxy, amino, mono- or di-$C_{1-4}$alkyl substituted amino, phenyl, benzyl or $C_{1-4}$alkyl optionally substituted by amino; and X is —CN, —NR$_5$R$_6$ or —O—R$_8$ wherein $R_5$ is H, $C_{1-6}$alkyl, aryl or aryl-$C_{1-4}$alkyl; $R_6$ is H or $C_{1-6}$alkyl; and $R_8$ is H, $C_{1-4}$alkyl, aryl or aryl-$C_{1-4}$alkyl; in free form or in salt form; which are useful in preventing or treating disorders or diseases mediated by LFA-1/ICAM-1, -ICAM-2 or -ICAM-3 interactions.

17 Claims, No Drawings

SUBSTITUTED 2-OXO-1,4-DIAZACYCLOALKANES

This application claims the benefit of U.S. provisional application No. 60/266,325 filed Oct. 13, 1999.

The present invention relates to diazepanes, a process for their production, their use as a pharmaceutical and pharmaceutical preparations containing them.

More particularly the present invention provides a compound of formula I

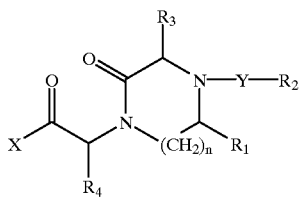

wherein
n is 1, 2 or 3,
$R_1$ is H, $C_{1-4}$ alkyl; aryl; or aryl-$C_{1-4}$alkyl,
Y is $C_{1-4}$alkylene; —CO—$C_{1-4}$alkylene; —CO—$C_{2-5}$alkenylene; —CO—NH—; —CO—$C_{1-3}$alkyle—NH—; or —CO—O—,
$R_2$ is an aromatic or heteroaromatic residue, each being optionally substituted by $CF_3$, halogen, OH, $C_{1-4}$alkoxy, amino, mono- or di-$C_{1-4}$alkyl substituted amino, phenyl, benzyl or $C_{1-4}$alkyl optionally substituted by amino,
$R_3$ is the side chain present on the C$\alpha$ of an a-amino acid,
$R_4$ is biphenylyl; or benzyl, hydroxy-benzyl, α- or β-naphthyl-methyl, 5,6,7,8-tetrahydro-β-naphthyl-methyl or indolyl-methyl, each being optionally substituted on the ring by $CF_3$, halogen, OH, $C_{1-4}$alkoxy, amino, mono- or di-$C_{1-4}$alkyl substituted amino, phenyl, benzyl or $C_{1-4}$alkyl optionally substituted by amino,
X is —CN; —$NR_5R_6$; or —O—$R_8$
$R_5$ is H, $C_{1-6}$alkyl, aryl or aryl-$C_{1-4}$alkyl,
$R_6$ is H or $C_{1-6}$alkyl and
$R_8$ is H, $C_{1-4}$alkyl, aryl or aryl-$C_{1-4}$alkyl,
in free form or in salt form.

Alkyl may be linear or branched. When alkyl is substituted by amino, it is preferably monosubstituted, more preferably terminally substituted. Aryl may be, e.g., optionally substituted phenyl, naphthyl or dihydro- or tetrahydro-naphthyl. Aryl-$C_{1-4}$alkyl may be, e.g., phenyl-$C_{1-4}$alkyl, e.g. benzyl, optionally substituted on the ring. Examples of substitutents are, e.g., halogen, OH, $CF_3$ or $NH_2$. Preferably aryl and aryl-$C_{1-4}$alkyl are unsubstituted.

Halogen may be F, Cl or Br.

When $R_2$ is an aromatic residue, it may be phenyl, naphthyl, dihydro- or tetrahydro-naphthyl or biphenylyl. Suitable heteroaromatic residues as $R_2$ include, e.g., pyridyl, quinolyl, isoquinolyl, dihydro-, tetrahydro-quinolyl or -isoquinolyl, e.g., 1,2,3,4-tetrahydro-quinolyl, benzo-thienyl, indolyl or pyridyl-phenyl. By optionally substituted tetrahydro-quinolyl or indolyl is also meant tetrahydro-quinolyl or indolyl wherein the nitrogen is substituted, e.g., by $C_{1-4}$alkyl, e.g., methyl or ethyl. When substituted, $R_2$ may be mono- or polysubstituted, e.g., disubstituted.

The α-amino acid or aromatic α-amino acid from which is derived the side chain present on the Cα as $R_3$, may be natural or non natural. Suitable examples as $R_3$ include, e.g., propyl, isopropyl, butyl, isobutyl, 1-methyl-propyl, phenyl, benzyl or aminobutyl.

By optionally ring substituted indolyl as $R_4$ is also meant indolyl wherein the nitrogen is substituted, e.g., by $C_{1-4}$alkyl, e.g. methyl or ethyl, or benzyl.

The compounds of formula I may exist in free form or in salt form, e.g., addition salts with, e.g., organic or inorganic acids, for example, hydrochloric acid, acetic acid, or salts obtainable when $R_8$ is H as salts with a base, e.g., alkali salts such as sodium or potassium, or substituted or unsubstituted ammonium salts.

It will be appreciated that the compounds of formula I may exist in the form of optical isomers, racemates or diastereoisomers as well as in the form of cis or trans conformers. For example, the carbon atom bearing the substituent $R_3$ or $R_4$, respectively, is asymmetric and may have the D- or L-configuration. For example, the carbon atom bearing $R_4$ has preferably the D-configuration when $R_4$ is α-naphthyl-methyl; it preferably has the L-configuration when $R_4$ is β-naphthyl-methyl. It is to be understood that the present invention embraces all enantiomers and conformers and their mixtures. Similar considerations apply in relation to starting materials exhibiting asymmetric carbon atoms as mentioned above.

In the compounds of formula I, the following significances are preferred individually or in any sub-combination:

1. n=2
2. Y is —$CH_2$—; —CO—$CH_2$—; —CO—$CH_2$—$CH_2$—; —CO—NH—; —CO—$CH_2$—NH—; or —CO—CH=CH—;
3. $R_1$ is $C_{1-4}$alkyl, preferably methyl or ethyl, more preferably methyl;
4. $R_1$ is $C_{1-4}$alkyl, preferably as indicated, and the carbon atom bearing it has the R- configuration;
5. $R_2$ is phenyl; phenyl substituted as indicated above, e.g. as indicated in the examples; naphthyl; pyridyl, preferably 2-, 3- or 4-pyridyl; pyridyl-phenyl; quinolyl, isoquinolyl, tetrahydro-quinolyl or substituted quinolyl or isoquinolyl, preferably 2-,4-, 6- or 8- quinolyl, optionally substituted as indicated above, e.g. as in the examples below;
6. $R_2$ is quinolyl or isoquinolyl; or substituted quinolyl or isoquinolyl, e.g., by OH, $OCH_3$ or phenyl; preferably quinolyl;
7. $R_3$ is isopropyl; n-butyl; isobutyl; or phenyl;
8. $R_4$ is α- or β-naphthyl-methyl;
9. $R_4$ is β-naphthyl-methyl and the carbon atom bearing $R_4$ has the L-(S)-configuration;
10. $R_4$ is β-naphthyl-methyl and the carbon atom bearing $R_4$ has the D-(R)-configuration;
11. X is —$NR_5R_6$;
12. $R_5$ is H; $C_{1-3}$alkyl; or benzyl;
13. $R_6$ is H or $CH_3$, preferably H.

The present invention also includes a process for the production of a compound of formula I, which process comprises appropriately substituting a corresponding compound of formula II as defined below, e.g., a) for the production of a compound of formula I wherein Y is —CO—$C_{1-4}$alkylene or —CO—$C_{2-5}$alkenylene, reacting a compound of formula II

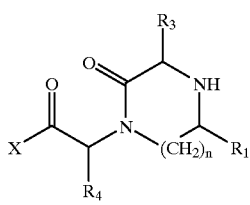

wherein $R_1$, $R_3$, $R_4$, X and n are as defined above, with a compound of formula IIIa $$R_2—Y'—OH \qquad \text{IIIa}$$

wherein $R_2$ is as defined above and Y' is —CO—$C_{1-4}$alkylene or —CO—$C_{2-5}$alkenylene or a functional derivative thereof;

b) for the production of a compound of formula I wherein Y is $C_{1-4}$alkylene, reacting a compound of formula II above, with a compound of formula IIIb:

$$R_2—Y''—CHO \qquad \text{IIIb}$$

wherein $R_2$ is as defined above and Y'' is a direct bond or $C_{1-3}$alkylene, under reducing conditions;

c) for the production of a compound of formula I wherein Y is —CO—NH— or —CO—$C_{1-3}$-alkylene-NH, reacting a compound of formula II above with a compound of formula IIIc:

$$X_1—CO—Y'''—X_2 \qquad \text{IIIc}$$

wherein Y''' is —CO—NH or —CO—$C_{1-3}$alkylene-NH and each of $X_1$ and $X_2$ is a leaving group, e.g., Br, and subsequently reacting the resulting compound with $R_2$—$NH_2$; and d) for the production of a compound of formula I wherein Y is —CO—NH—, reacting a compound of formula II with $R_2$—N=C=O, and, where required, converting the resulting compound of formula I obtained in free form to a salt form or vice versa.

A functional derivative of a compound of formula IIIa includes, e.g., a halide, ester or anhydride.

Process step a) may be carried out according to known acylation methods, e.g., in liquid phase or in solid phase. The latter case may particularly be suitable for the preparation of a compound of formula I wherein X is $NR_5R_6$: in such a case, the compound of formula II is attached to a resin, e.g., a commercially available resin, e.g. by NH. Once acylation is complete, the desired compound of formula I is cleaved from the resin, e.g., by acidic hydrolysis.

Process step b) may be carried out according to known methods, in the presence of a reducing agent, e.g., NaCNBH$_3$. Process steps c) and d) may be performed according to known methods.

The compounds of formula II may be produced, e.g., by cyclisation of a compound of formula IV:

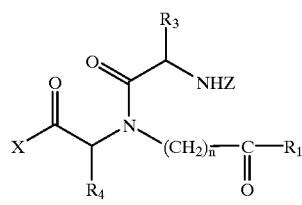

wherein $R_1$, $R_3$, $R_4$, X and n are as defined above and Z is an amino protecting group, in the presence of a reducing agent.

Suitable reducing agents include, e.g., NaCNBH$_3$, Na BH(CH$_3$COO)$_3$, or Na triacetoxy borohydride. The compounds of formula II may be prepared in liquid or solid phase. In the latter case, the compound of formula IV is attached to a resin by an appropriate group X', e.g. NH. Suitable N-protecting groups may be, e.g., as disclosed in "Protective Groups in Organic Synthesis," T. W. Greene, J. Wiley & Sons NY(1981), 219–287, e.g., alcoxycarbonyl such as methoxycarbonyl or t-butyloxycarbonyl, allyloxycarbonyl, arylmethoxycarbonyl such as Fmoc, or benzyloxycarbonyl.

Insofar as the production of the starting materials is not particularly described, the compounds are known or may be prepared analogously to methods known in the art or as disclosed hereafter.

The following Examples are illustrative of the invention.

In the following examples:

Fmoc=9-Fluorenyl methoxy carbonyl

Boc=tert.-butoxy-carbonyl

RT=room temperature

THF=tetrahydrofurane

TFA=trifluoroacetic acid

DMF=dimethylformamide

DCCl=dicyclohexylcarbodiimide

EADC=N-(3-dimethylaminopropyl)-N'-ethylcarbodiimide hydrochloride

NMM=N-methyl morpholine

DIPCl=diisopropylcarbodiimide

HOBt=hydroxy benzotriazole

DIPEA=diisopropyl ethyl amine, also called Hünig's base

AcOH=acetic acid

Nal=naphthyl-alanine

Phg=phenyl-glycine

Example 1: (S)-2-[(3S,5R)-3-Isobutyl-5-methyl-2-oxo-4-(quinolin-6-yl-acetyl)-[1,4]diazepan-1-yl]-3-(naphthalen-2-yl)-propionamide

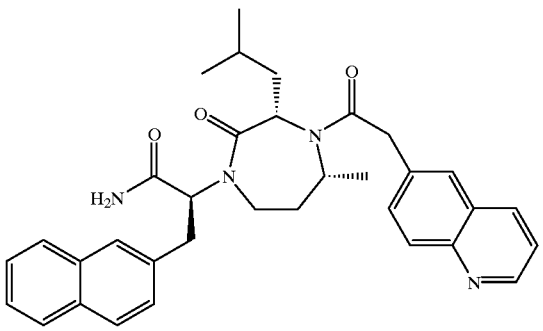

(S)-2-[(3S,5R)-3-isobutyl-5-methyl-2-oxo-[1,4]diazepan-1-yl]-3-(naphthalen-2-yl)-propionamide (382 mg, 1 mmol) is added to a solution of 6-quinolylacetic acid (372 mg, 2 mmol), Hünig's base (170 µl, 1 mmol) and EADC (383 mg, 2 mmol) in $CH_2Cl_2$ (50 ml). After 16 hours at RT the reaction mixture is extracted with 0.1 N HCl and then with 5% $NaHCO_3$ solution. Pure title compound is isolated after silica gel chromatography using ethyl acetate —>ethyl acetate/MeOH (9/1) as mobile phase. $MH^+$:551.4 (ESI) $\alpha_D^{20}$=−12.5° (c=0.12 95% AcOH)

(S)-2-[(3S,5R)-3-isobutyl-5-methyl-2-oxo-[1,4]diazepan-1-yl]-3-(naphthalen-2-yl)-propionamide, used as starting material, may be prepared as follows:

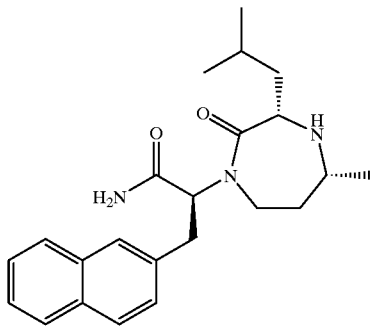

a) N-Boc-β-L-NaI—$NH_2$:

DCCl (5.0 g, 24 mmol) is added to a solution of N-Boc-β-L-NaI—OH (6.3 g, 20 mmol), HOBt (3.7 g, 24 mmol) and $NH_4OH$ (25%) (2.0 ml, 24 mmol) in DMF (100 ml) at RT. After 16 hours at RT the solution is filtered and poured into 2 liter 5% aqueous $NaHCO_3$ solution. The resulting precipitate is filtered off and is dissolved in ethyl acetate (500 ml). After drying over $Na_2SO_4$ the solvent is removed under reduced pressure. The title compound forms an amorphous solid from c-hexane.

b) H-β-L-NaI—$NH_2$.HCl:

N-Boc-β-L-NaI-$NH_2$ (6.215 g, 20 mmol) is treated with 60 ml neat TFA at 0° C. for 15 minutes. After that the clear solution is poured into 2 l diethylether containing 100 ml of a 3N HCl/diethylether solution. The resulting precipitate is filtered off and is dried at 40° C. for 2 hours.

c) $N^α$-(3-oxo-butyl)-β-L-NaI-$NH_2$:

H-β-L-NaI—$NH_2$.HCl (4.3 g, 17 mmol) is dissolved in 200 ml dioxane at room temperature. After addition of Hünig's base (3.4 ml; 20 mmol) and methylvinylketone (25 ml, 300 mmol) the reaction is kept at room temperature for 16 hours. The reaction is concentrated to 100 ml and the remaining solution is poured into methyl-tert.-butylether (4 l). The precipitate is filtered off, then washed and is used for the next step without further purification.

d) $N^α$-Boc-Leu-$N^α$-(3-oxo-butyl)-β-L-NaI—$NH_2$:

$N^α$-(3-oxo-butyl)-β-L-NaI—NH2 (4.5 g, 16 mmol) is added to a solution of Boc-Leu-OH=$H_2O$ (14.8 g, 64 mmol), NMM (3.1 ml, 64 mmol) and DIPCl (5 ml, 64 mmol) in DMF (100 ml). The reaction is kept at RT for 16 hours, filtered and then poured into 2 liter 5% aqueous $NaHCO_3$. The aqueous phase is decanted and the sticky residue is dissolved in ethyl acetate and dried over $Na_2SO_4$. Purification is achieved by silica gel chromatography using ethyl acetate —>ethyl acetate/MeOH (9/1) as mobile phase.

e) H-Leu-$N^α$-(3-oxo-butyl)-β-L-NaI—$NH_2$.HCl:

$N^α$-Boc-Leu-$N^α$-(3-oxo-butyl)-β-L-NaI—$NH_2$ (2.9 g, 6 mmol) is treated with 30 ml neat TFA at 0° C. for 15 minutes. After that the clear solution is poured into 1 l diethylether containing 50 ml of a 3N HCl/diethylether solution. The resulting precipitate is filtered off and is dried at 40° C. for 2 hours.

f) (S)-2-[(3S,5R)-3-isobutyl-5-methyl-2-oxo-[1,4]diazepan-1-yl]-3-(naphthalen-2-yl )-propionamide H-Leu-$N^α$-(3-oxo-butyl)-β-L-NaI—$NH_2$.HCl (2.5 g, 6 mmol) is dissolved in dioxane/water (4/1, 100 ml) and the pH is adjusted to 5.4 with 1 N aqueous NaOH. The cyclization reaction is carried out with $NaCNBH_3$ (0.79 g, 12 mmol) at RT. After 30 minutes reaction time most of the dioxane is removed under reduced pressure and the aqueous phase is extracted 3 times with ethyl acetate. Pure endproduct is obtained after silica gel chromatography using ethyl acetate —> ethyl acetate/MeOH (9/1) as mobile phase. $MH^+$:382.2 (ESI) $\alpha_D^{20}$:−46.9 (c=0.18 95% AcOH)

Example 2: (S)-2-[(3S,5R)-3-isobutyl-5-methyl-2-oxo4-(quinolin-6-yl-acetyl)-[1,4]diazepan-1-yl]-N-methyl-3-(naphthalen-2-yl)-propionamide

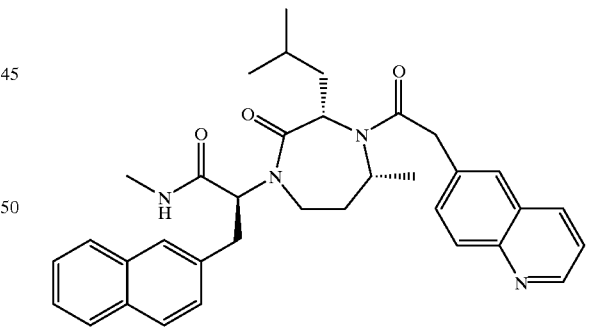

The title compound is obtained by following the procedure of Example 1 and starting with (S)-2-[(3S,5R)-3-isobutyl-5-methyl-2-oxo-[1,4]diazepan-1-yl]-N-methyl-3-(naphthalen-2-yl )-propionamide instead of (S)-2-[(3S,5R)-3-isobutyl-5-methyl-2-oxo-[1,4]diazepan-1-yl]-3-(naphthalen-2-yl)-propionamide. $MH^+$:565.4 (ESI) $\alpha_D^{20}$:+19.9° (c=0.18 95% AcOH) (S)-2-[(3S,5R]-3-Isobutyl-5-methyl-2-oxo-[1,4]diazepan-1-yl]-N-methyl-3-(naphthalen-2-yl)-propionamide

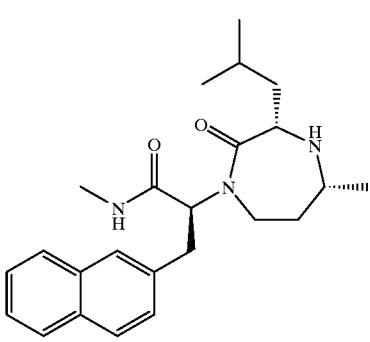

used as starting material may be prepared as disclosed in Example 1, steps (a) to (f) but employing methylamine-hydrochloride (1.4 g, 24 mmol) and NMM (2.6 ml, 24 mmol) instead of $NH_4OH$ (25%) in step a). $MH^+$:396.0 (ESI) $\alpha^{20}_D$:−67.0° (c=0.50 95% AcOH)

Example 3: (R)-2-[(3S,5R)-5Methyl-2-oxo-3-phenyl-4-(quinolin-6-yl-acetyl)-[1,4]diazepan-1-yl]-3-(naphthalen-1-yl)-propionamide

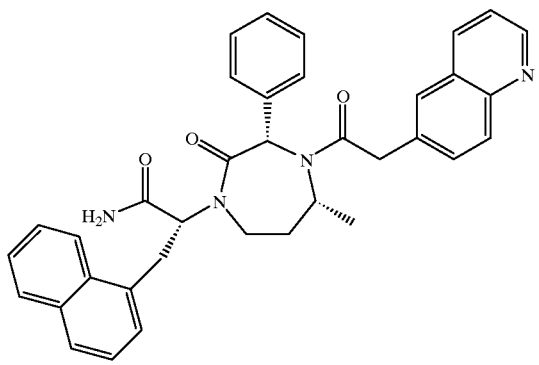

The title compound is prepared by following the procedure of Example 1 but starting from (R)-2-[(3S,5R)-5-methyl-2-oxo-3-phenyl-[1,4]-diazepan-1-yl]-3-(naphthalen-1-yl)-propionamide and using Boc-α-D-Nal—OH in step a) instead of N-Boc-β-L-Nal—OH and Boc-L-Phg—OH in step d) instead of Boc-Leu—OH. $MH^+$: 571 ($ES^+$) $\alpha_D^{20}$+ 187.6 (c=0.15 95% AcOH)

Example 4: (S)-2-[(3S,5R)-3-Isobutyl-5-methyl-2-oxo4-((β-naphthyl-acetyl)-[1,4]diazepan-1-yl]-3-(naphthalen-2-yl)-propionamide

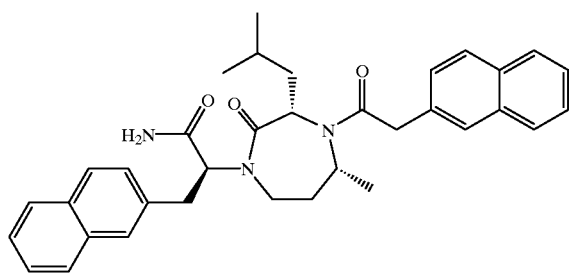

a) Commercially available Fmoc-Rink-amide MBHA resin (0.61 mmol/g, 1 eq.) is washed with isopropanol (1×), DMF (2×), and then treated with a 20% solution of piperidine in DMF (4×5 min). The resin is then washed with DMF (1×), isopropanol (2×) and DMF (4×). In a separated vessel, the Fmoc-β-L-Nal—OH (6 eq.) is activated by the sequential addition of a 0.5 M solution of HOBt (6 eq.) in DMF and a 2 M solution of DIPCl (6 eq.). After stirring for 10 min. this solution is transferred to the resin. DIPEA (1 eq.) is added to the suspension of resin which is shaken over night at RT. The shaking vessel is then drained and the resin is washed with DMF (4×), EtOH (2×), $CH_2Cl_2$ (3×), EtOH (2×), $CH_2Cl_2$ (3×) and dried over a $N_2$ stream. The resulting resin gives a negative result (yellow color) with the bromophenol blue test and the loading of the resin is controlled by Fmoc titration after treatment of 2–5 mg of resin with 20% piperidine in DMF.

b) The resin is washed with isopropanol (1×), DMF (2×), and then treated with a 20% solution of piperidine in DMF (4×5 min). The resin is then washed with DMF (1×), isopropanol (2×) and DMF (4×). A 0.5 M solution of methyl vinylketone in DMF is then added and the resulting suspension is shaken over night at RT. The shaking vessel is then drained and the resin is washed with DMF (4×), $CH_2Cl_2$ (3×), DMF (2×), $CH_2Cl_2$ (2×) and DMF (3×). The resulting resin gives a positive result (deep blue color) with the bromophenol blue test and is used directly in the next step without drying.

c) The resin is washed with DMF (2×). A 0.5 M solution of Fmoc-Leu—OH (10 eq.) in DMF is then added followed by DIPCl (5 eq.). The resulting suspension is shaken for 48 h at RT. The shaking vessel is drained and the resin is washed with DMF (4×), EtOH (2×), $CH_2Cl_2$ (3×), EtOH (2×), $CH_2Cl_2$ (3×) and is dried over a $N_2$ stream. Under completion, the resulting resin gives a negative result (yellow color) with the bromophenol blue test. The reaction is re-runned when a positive result (deep blue color) is obtained.

d) The resin is washed with DMF (1×) and then treated with a 20% solution of piperidine in DMF (4×5 min). The resin is washed with DMF (2×), $CH_2Cl_2$ (2×), DMF (4×) and then treated with a 0.5 M solution of $NaBH_3CN$ (10 eq.) in 1% AcOH buffered DMF. After over night shaking at RT, the vessel is drained and the resin is washed with 1% AcOH/DMF (4×), MeOH (4×), $CH_2Cl_2$ (3×), MeOH (3×), $CH_2Cl_2$ (4×) and dried over a N stream. The resulting resin gives a positive result (deep blue color) with the bromophenol blue test.

e) The resin is washed with DMF (2×). A 0.4 M pre-mixed solution of β-naphthylacetic acid (10 eq.) and DIPCl (10 eq.) is then added followed by DIPEA (2 eq.). After over night shaking, the vessel is drained and the resin is washed with DMF (4×), $CH_2Cl_2$ (3×), DMF (2×), $CH_2Cl_2$ (4×). The resin is then treated with 50% $TFA/CH_2Cl_2$ and shaken at RT for 60 min. The resin is washed with 50% $TFA/CH_2Cl_2$ (1×), $H_2O$ (2×), $CH_2Cl_2$ (3×) and the filtrate is concentrated using a $N_2$ stream. The residue is dissolved in a small amount of ethyl acetate and then purified on a short silica gel column using ethyl acetate →ethyl acetate/methanol (1/1) as mobile phase. Fractions containing the title compound are concentrated and taken then into $CH_3CN/H_2O$ ⅓ and freeze dried to give a white powder. White powder;, Rt 18.25 min (HPLC RP $C_{18}$, 0–100% $CH_3CN$ in $H_2O$/20 min); MS m/z (relative intensity) (ESI) 533 (100), 550 (73), 572 (10); Anal. Calcd for $C_{35}H_{39}N_3O_3$: C 76.47, H 7.15, N 7.64; Found: C 76.18, H 7.12, N 7.76.

Example 5: (S)-2-[(3S,5R)-3-Isobutyl-5-methyl-2-oxo4-(β-naphthyl-acetyl)-[1,4]diazepan-1-yl]-3-(naphthalen-2-yl)-propionic acid

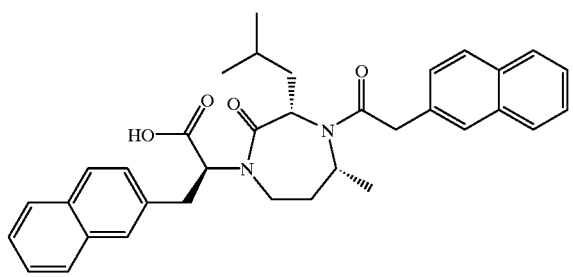

This compound is isolated during the purification on silica gel of the compound of Example 4.

The compounds of formula X:

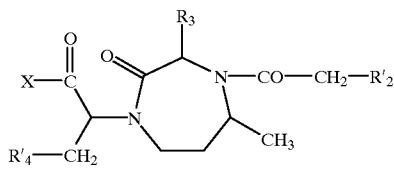

X wherein R'$_2$, R$_3$, R'$_4$ and X are as defined in Table 1 below, may be prepared by following the procedures of Examples 1 and 4 and using the appropriate starting materials.

TABLE 1

| Ex | R'$_2$ | R$_3$ | R'$_4$ | X | MH + (ESI) |
|---|---|---|---|---|---|
| 6 | β-naphthyl | n-butyl | β-naphthyl | NH$_2$ | 550.3 |
| 7 | Phenyl | isobutyl | β-naphthyl | NH$_2$ | 500.3 |
| 8 | 4-pyridyl | isobutyl | β-naphthyl | NH$_2$ | 501.3 |
| 9 | 6-quinolyl | isobutyl | α-naphthyl | NH$_2$ | 551.3 |
| 10 | 3-quinolyl | isobutyl | β-naphthyl | NH$_2$ | 551.3 |
| 11 | 6-quinolyl | isobutyl | β-naphthyl | OCH$_3$ | 566.3 |
| 12 | 6-quinolyl | isobutyl | β-naphthyl | NH-benzyl | 641.4 |
| 13 | β-naphthyl | isobutyl | β-naphthyl | NHCH$_3$ | 564.3 |
| 14 | 4-Bromo-phenyl | isobutyl | β-naphthyl | NH$_2$ | 580.3 |
| 15 | β-naphthyl | phenyl | α-naphthyl | NH$_2$ | 568.3 |
| 16 | 3-indol-3-yl | isobutyl | β-naphthyl | NH$_2$ | 539.4 |
| 17 | N—CH$_3$-indol-3-yl | isobutyl | β-naphthyl | NH$_2$ | 553.4 |
| 18 | p-(3-pyridyl)-phenyl | isobutyl | β-naphthyl | NH$_2$ | 577.4 |
| 19 | 6-quinolyl | isobutyl | 5,6,7,8-tetrahydro-β-naphthyl | NH$_2$ | 555.4 |
| 20 | 3,4-dichloro-phenyl | phenyl | α-naphthyl | NH$_2$ | 488.0 |
| 21 | 6-quinolyl | isobutyl | 4-bromo-phenyl | NH$_2$ | 579/581 |
| 22 | p-amino-phenyl- | isobutyl | α-naphthyl | NH$_2$ | 551.3 |
| 23 | p-(NH$_2$—CH$_2$)-phenyl- | isobutyl | α-naphthyl | NH$_2$ | 529.4 |
| 24 | 6-quinolyl | isobutyl | α-naphthyl | NH$_2$ | 551 |
| 25 | p-[di(CH$_3$)-amino]-phenyl | isobutyl | α-naphthyl | NH$_2$ | 543 |
| 26 | p-chloro-phenyl | isobutyl | α-naphthyl | NHCH$_3$ | 549 |
| 27 | p-ethoxy-phenyl | isobutyl | α-naphthyl | NHCH$_3$ | 558 |
| 28 | 1-CH$_3$-1,2,3,4-tetrahydro-6-quinolyl | isobutyl | α-naphthyl | NHCH$_3$ | 583 |
| 29 | 3-bromo-5-pyridyl | isobutyl | α-naphthyl | NH$_2$ | 580 |
| 30 | 4-quinolyl | isobutyl | β-naphthyl | NHCH$_3$ | 564 |
| 31 | 7-CH$_3$O-3-quinolyl | isobutyl | β-naphthyl | NHCH$_3$ | 595.4 |
| 32 | 2-phenyl-6-quinolyl | isobutyl | β-naphthyl | NHCH$_3$ | 641 |
| 33 | 1-OH-3-isoquinolyl | isobutyl | β-naphthyl | NHCH$_3$ | 581 |
| 34 | 3,4-di(CH$_3$O)-phenyl | isobutyl | β-naphthyl | NHCH$_3$ | 574 |
| 35 | 3-CH$_3$O-4-OH-phenyl | isobutyl | β-naphthyl | NHCH$_3$ | 560 |
| 36 | β-naphthyl | phenyl | α-naphthyl | CN | 560.3 |

The compounds of formula XI:

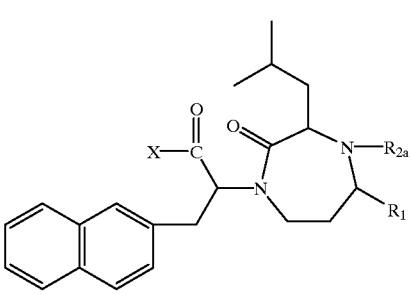

XI wherein R$_{2a}$, R$_1$ and X are as defined in Table 2 below, may be prepared by following the procedures of Examples 1 and 4 and using the corresponding starting materials.

TABLE 2

| Ex | R$_{2a}$ | R$_1$ | X | MH + (ESI) |
|---|---|---|---|---|
| 37 | 4-quinolyl-CH$_2$—CH$_2$—CO- | CH$_3$ | NH$_2$ | 565.4 |
| 38 | 6-quinolyl-CH$_2$—CO- | CH$_2$CH$_3$ | NH$_2$ | 565.4 |
| 39 | 4-quinolyl-CH=CH—CO- | CH$_3$ | NH$_2$ | 563.0 |
| 40 | 4-quinolyl-CH=CH—CO- | CH$_3$ | NHCH$_3$ | 577.4 |
| 41 | α-naphthyl-CH=CH—CO- | CH$_3$ | NHCH$_3$ | 562.2 |
| 42 | 4-pyridyl-CH=CH—CO- | CH$_3$ | NHCH$_3$ | 513.0 |
| 43 | benzyl[a] | CH$_3$ | NHCH$_3$ | 486 |
| 44 | phenyl-NHCO-[b] | CH$_3$ | NHCH$_3$ | 515 |
| 45 | β-naphthyl-NHCO-[b] | CH$_3$ | NHCH$_3$ | 565 |
| 46 | (p-F-phenyl)-NH—CH$_2$—CO- | CH$_3$ | NHCH$_3$ | 547 |

[a]prepared according to process step b)
[b]prepared according to process step c)

The compounds of Examples 1 to 46 may also be prepared as R- or S-enantiomers or as mixtures as regards the carbon atoms bearing the substitutents R$_1$ (when this is other than H), R$_3$ and R$_4$, respectively.

The compounds of formula I, in free form or in pharmaceutically acceptable salt form, exhibit valuable pharmacological properties, e.g., inhibiting activity of LFA-1/ICAM-1, -ICAM-2 or -ICAM-3 interactions or inhibiting inflammation, e.g., as indicated in in vitro and in vivo tests and are therefore indicated for therapy.

A. In vitro: Cell Free Assay

The assay measures the binding of soluble human ICAM-1 to immobilized human LFA-1. LFA-1 is purified from JY cells, a human lymphoblastoid B cell-line, by immunoaffinity chromatography as described by Dustin et al. (J. Immunol. 148, 2654–2663, 1992). ICAM-1 mouse CK fusion protein (ICAM-1) is produced using the baculovirus system as described by Weitz-Schmidt et al. (Anal. Biochem.238, 184–190, 1996).

Purified LFA-1 is diluted 1:20 in phosphate buffered saline (PBS) containing 2 mM MgCl2, pH 7.4 and coated onto; microtitre plates (Nunc) at 37° C. for 3h. Plates are blocked with 1% heat-treated BSA in PBS for 2 hours at 37° C. followed by a washing step using PBS, 2mM MgCl$_2$, 1% fetal calf serum, pH 7.4 (assay buffer). Compounds dissolved at 10 mM in DMSO are diluted in assay buffer and added to the plates. Biotinylated recombinant ICAM-1 in assay buffer (6 μg/ml) is added and allowed to bind at 37° C. for one hour. After incubation, wells are washed with assay buffer. Streptavidin-peroxidase diluted 1:5000 in assay buffer is added and incubated for 45 min at 37° C. Plates are then washed with assay buffer and 2.2'-azino-bis(3-ethylbenzothiazoline-6 sulfonic acid) diammonium salt substrate solution is added to each well. The reaction is stopped after 20 min and bound ICAM-1 is determined by measuring the optical density at 405 nm in a microplate reader.

In this assay, compounds of formula I inhibit adhesion of LFA-1 to ICAM-1 with an $IC_{50} \leq 30$ µM, preferably 0.05 to 30 µM. Compounds of Examples 1 and 3 have an $IC_{50}$ of 0.44 and 0.07 µM, respectively, in this assay.

B. In vivo i) Murine Thioglycollate Induced Peritonitis

Thioglycolate is injected i.p. to mice and immediately thereafter the compound to be tested is given s.c. The mice are killed after 4 hours, the peritoneal cavity lavaged and total number of neutrophils in the lavage fluid is determined.

In this assay, the compounds of formula I inhibit thioglycolate induced neutrophil migration when administered p.o. at a dose of from 0.001–50 mg/kg either at the time of thioglycolate injection or 3 hours before.

ii) Allergic Contact Dermatitis (ACD)

Groups of 8 female NMRI mice are sensitized on the shaved abdomen with 50 —l of oxazolone (Sigma, 2% in acetone) and challenged with 10 —l of 0.2 or 2.0% oxazolone on the inner surface of the right ear 7 days later. The low concentration of oxazolone for induction of the elicitation phase is used for testing compounds on systemic activity whereas the high concentration is applied for systemic testing. The unchallenged left ears serve as normal controls and dermatitis is evaluated from the individual differences in pinnal weight, which is taken as a measure of increase in inflammatory swelling 24 h after the challenge. Dermatitis is evaluated in test- and for comparison in control groups. The test groups are treated with the test compounds either orally (twice, 2 h and immediately before challenge), subcutaneously (immediately before challenge) or topically (30 min after challenge at the site of elicitation of the ACD); the controls are treated similarly with the vehicles alone. For oral and subcutaneous administration the compounds are administered in an oil in water emulsion, for topical administration the compounds are prepared in a mixture of ethanol, acetone and dimethylacetamide. The data of the test-and the vehicle-treated control groups are statistically analysed by ANOVA followed by Dunnet T-test (normal distribution or data) or by H and U-test, respectively. When administered p.o. at a dose of from 0.1 to 10 mg/kg, compounds of formula I inhibit the elicitation phase of allergic contact dermatitis. The compound of Example 3 has an inhibiting effect in this assay of 40% when administered p.o. at a dose of 2×3 mg/kg, or of 50% when applied topically at a dose of 10 mM.

The compounds of formula I are, therefore, useful in the treatment and/or prevention of diseases or disorders mediated by LFA-1/ICAM-1, -ICAM-2 or -ICAM-3 interactions, e.g., ischemia/reperfusion injury e.g. myocardial infarction, stroke, gut ischemia, renal failure or hemorrhage shock, acute or chronic rejection of organ or tissue allo- or xenografts, cancer, infection diseases such as septic shock, adult respiratory distress syndrome, or traumatic shock.

The compounds of formula I are also useful in the treatment and/or prevention of acute or chronic inflammatory diseases or disorders or autoimmune diseases, e.g., rheumatoid arthritis, osteoarthritis, systemic lupus erythematosus, hashimoto's thyroidis, multiple sclerosis, myasthenia gravis, diabetes type I and uveitis, asthma, inflammatory lung injury, inflammatory liver injury, inflammatory glomerular injury, cutaneous manifestations of immunologically-mediated disorders or illnesses, inflammatory and hyperproliferative skin diseases, (such as psoriasis, atopic dermatitis, alopecia aerata, allergic contact dermatitis, irritant contact dermatitis and further eczematous dermatitises, seborrhoeic dermatitis, lichen planus, pemphigus, bullous pemphigoid, epidermolysis bullosa, urticaria, angioedemas, vasculitides, erythema multiforme, cutaneous eosinophilias, lupus erythematbsus, acne, granuloma annulare, pyoderma gangrenosum, sun burns or toxic epidermal necrolysis), inflammatory bowel disease, Crohn's disease, ulcerative colitis, ophthalmic inflammatory diseases or immune-mediated conditions of the eye, such as autoimmune diseases, e.g., keratoplasty and chronic keratitis, allergic conditions, e.g. vernal conjunctivitis, inflammatory conditions and corneal transplants.

For the above uses the required dosage will of course vary depending on the mode of administration, the particular condition to be treated and the effect desired. In general, satisfactory results are indicated to be obtained systemically at daily dosages of from about 0.1 to about 100 mg/kg body weight. An indicated daily dosage in the larger mammal, e.g., humans, is in the range from about 0.5 mg to about 500 mg, conveniently administered, for example, in divided doses up to four times a day or in retard form.

For topical use satisfactory results are obtained with local administration of a 1–3% concentration of active substance several times daily, e.g., 2 to 5 times daily.

The compounds of formula I may be administered systemically or topically, by any conventional route, in particular enterally, e.g., orally, e.g. in the form of tablets or capsules, topically, e.g., in the form of lotions, gels, ointments or creams, or in a nasal or a suppository form. Percutaneous administration via patches or other delivery systems may also be a possible route for prevention or treatment of above diseases.

Pharmaceutical compositions comprising a compound of formula I in free form or in pharmaceutically acceptable salt form in association with at least one pharmaceutical acceptable carrier or diluent may be manufactured in conventional manner by mixing with a pharmaceutically acceptable carrier or diluent. Unit dosage forms for oral administration contain, for example, from about 0.1 mg to about 125 mg of active substance.

Topical administration is, e.g., to the skin. A further form of topical administration is to the eye.

The compounds of formula I may be administered in free form or in pharmaceutically acceptable salt form e.g. as indicated above. Such salts may be prepared in conventional manner and exhibit the same order of activity as the free compounds.

In accordance with the foregoing the present invention further provides:

1.1 A method for preventing or treating disorders or diseases mediated by LFA-1/ICAM-1, -ICAM-2 or-ICAM-3 interactions, e.g., such as indicated above, in a subject in need of such treatment, which method comprises administering to said subject an effective amount of a compound of formula I or a pharmaceutically acceptable salt thereof;

1.2 A method for preventing or treating acute or chronic inflammatory diseases or disorders or autoimmune diseases, e.g., as indicated above, e.g., psoriasis or other inflammatory skin diseases, in a subject in need of such treatment, which method comprises administering to said subject an effective amount of a compound of formula I or a pharmaceutically acceptable salt thereof;

2. A compound of formula I, in free form or in a pharmaceutically acceptable salt form for use as a pharmaceutical, e.g., in any of the methods as indicated under 1.1 and 1.2 above.

3. A pharmaceutical composition for use in any of the methods as in 1.1 and 1.2 above comprising a compound of formula I in free form or pharmaceutically acceptable salt form in association with a pharmaceutically acceptable diluent or carrier therefor.

4. A compound of formula I or a pharmaceutically acceptable salt thereof for use in the preparation of a pharmaceutical composition for use in any of the methods as in 1.1 and 1.2 above.

The compounds of formula I may be administered as the sole active ingredient or together with other drugs in immunomodulating regimens or other anti-inflammatory agents for the treatment or prevention of allo- or xenograft acute or chronic rejection or inflammatory or autoimmune disorders. For example, they may be used in combination with cyclosporins, rapamycins or ascomycins, or their immunosuppressive analogs, e.g. cyclosporin A, cyclosporin G, FK-506, ABT-281, ASM 981, rapamycin, 40-O-(2-hydroxy) ethyl-rapamycin etc.; corticosteroids; cyclophosphamide; azathioprene; methotrexate; FTY 720; leflunomide; mizoribine; mycophenolic acid; mycophenolate mofetil; 15-deoxyspergualine; immunosuppressive monoclonal antibodies, e.g., monoclonal antibodies to leukocyte receptors, e.g., MHC, CD2, CD3, CD4, CD7, CD25, CD28, B7, CD40, CD45, or CD58 or their ligands (e.g., CD154); or other immunomodulatory compounds, e.g., CTLA4lg, or other adhesion molecule inhibitors, e.g. mAbs or low molecular weight inhibitors including Selectin antagonists and VLA-4 antagonists.

Where the compounds of formula I are administered in conjunction with other immunosuppressive/immunomodulatory or anti-inflammatory therapy, e.g., for preventing or treating acute or chronic rejection or inflammatory or autoimmune disorders as hereinabove specified, dosages of the co-administered immunosuppressant, immunomodulatory or anti-inflammatory compound will of course vary depending on the type of co-drug employed, e.g. whether it is a steroid or a cyclosporin, on the specific drug employed, on the condition being treated and so forth. In accordance with the foregoing the present invention provides in a yet further aspect:

5. A method as defined above comprising co-administration, e.g., concomitantly or in sequence, of a therapeutically effective amount of a compound of formula I in free form or in pharmaceutically acceptable salt form, and a second drug substance, said second drug substance being an immunosuppressant, immunomodulatory or anti-inflammatory drug, e.g., as indicated above.

6. A therapeutic combination, e.g., a kit, for use in any method as defined under 1.1 or 1.2 above, comprising a compound of formula I, in free form or in pharmaceutically acceptable salt form, to be used concomitantly or in sequence with at least one pharmaceutical composition comprising an immunosuppressant, immunomodulatory or anti-inflammatory drug. The kit may comprise instructions for its administration.

A preferred compound according to the invention is the compound of Example 3.

What is claimed is:

1. A compound of formula I

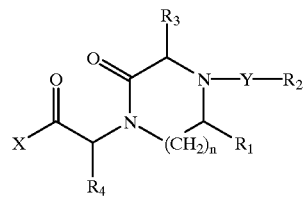

wherein n is 2;

$R_1$ is H, $C_{1-4}$alkyl, aryl, or aryl-$C_{1-4}$alkyl;

Y is $C_{1-4}$alkylene, —CO—$C_{1-4}$alkylene, —CO—$C_{2-5}$alkenylene, —CO—NH—, —CO—$C_{1-3}$alkylene-NH—, or —CO—O—;

$R_2$ is phenyl, naphthyl, dihydro- or tetrahydro-naphthyl, biphenylyl, pyridyl, quinolyl, isoquinolyl, dihydro- or tetrahydro-quinolyl or -isoquinolyl, benzo-thienyl, indolyl or pyridyl-phenyl, each being optionally substituted by $CF_3$, halogen, OH, $C_{1-4}$alkoxy, amino, mono- or di-$C_{1-4}$alkyl substituted amino, phenyl, benzyl or $C_{1-4}$alkyl optionally substituted by amino;

$R_3$ is propyl, isopropyl, butyl, isobutyl, 1-methylpropyl, phenyl, benzyl or aminobutyl;

$R_4$ is biphenylyl, benzyl, hydroxy-benzyl, α- or β-naphthyl-methyl, 5,6,7,8-tetrahydro-β-naphthyl-methyl or indolyl-methyl, each being optionally substituted on the ring by $CF_3$, halogen, OH, $C_{1-4}$alkoxy, amino, mono- or di-$C_{1-4}$alkyl substituted amino, phenyl, benzyl or $C_{1-4}$alkyl optionally substituted by amino; and X is —CN, —$NR_5R_6$, or —O—R8 Wherein $R_5$ is H, $C_{1-6}$alkyl, aryl or aryl-$C_{1-4}$alkyl; $R_6$ is H or $C_{1-6}$alkyl; and $R_8$ is H, $C_{1-4}$alkyl, aryl or aryl-$C_{1-4}$alkyl; or a pharmaceutically acceptable salt thereof.

2. A compound according to claim 1 wherein $R_1$ is $C_{1-4}$alkyl; and $R_2$ is naphthyl, quinolyl, tetrahydro-quinolyl, tetrahydro-1-methyl-quinolyl, or quinolyl substituted by OH, $OCH_3$ or phenyl.

3. A compound according to claim 1, wherein $R_4$ is α- or β-naphthyl-methyl.

4. A compound according to claim 3 wherein $R_1$ is $C_{1-4}$alkyl; $R_3$ is isopropyl, butyl, isobutyl or phenyl; and R4 is α- or β-naphthylmethyl.

5. A compound according to claim 4 wherein X is $NR_5R_6$ in which $R_5$ is H, $C_{1-3}$alkyl or benzyl, and $R_6$ is H or $CH_3$.

6. (R)-2-[(3S,5R)-5-Methyl-2-oxo-3-phenyl-4-(quinolin-6-yl-acetyl)-[1,4]diazepan-1-yl]-3-(naphthalen-1-yl)-propionamide; or a pharmaceutically acceptable salt thereof.

7. A process for the preparation of a compound of formula I according to claim 1, wherein Y is $C_{1-4}$alkylene, —CO—$C_{1-4}$alkylene, —$COC_{2-5}$alkenylene, —CONH—and $COC_{1-3}$alkylene-NH, which process comprises appropriately N-substituting a corresponding compound of formula II

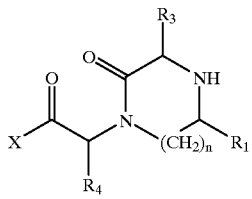

wherein $R_1$, $R_3$, $R_4$, X and n are as defined in claim 1, a) for the preparation of a compound of formula I wherein Y is —CO—$C_{1-4}$alkylene or —CO—$C_{2-5}$alkenylene, by reacting a compound of formula II above with a compound of formula IIIa

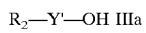

wherein $R_2$ is as defined in claim 1 and Y' is —CO—$C_{1-4}$alkylene or —CO—$C_{2-5}$alkenylene, or a functional derivative thereof; or b) for the preparation of a compound of formula I wherein Y is $C_{1-4}$alkylene, by reacting a compound of formula II above with a compound of formula IIIb

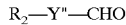

wherein $R_2$ is as defined in claim 1 and Y" is a direct bond or $C_{1-3}$alkylene, in the presence of a reducing agent; or c) for the production of a compound of formula I wherein Y is —CO—NH—or —CO—$C_{1-3}$-alkylene-NH, by reacting a compound of formula II above with a compound of formula IIIc wherein Y'" is —CO—NH or —CO—$C_{1-3}$alkylene-NH and each of $X_1$ and $X_2$ is a leaving group, and subsequently reacting the resulting compound with $R_2$—$NH_2$, wherein $R_2$ is as defined in claim 1; or d) for the preparation of a compound of formula I wherein Y is —CO—NH—, by reacting a compound of formula II with a compound of the formula $R_2$-N=C=O, wherein $R_2$ is as defined in claim 1; and e) where required, converting the resulting compound of formula I obtained in free form to a salt form or vice versa.

8. A pharmaceutical composition comprising a compound according to claim 1 in combination with a pharmaceutically acceptable diluent or carrier.

9. A pharmaceutical composition comprising a compound of claim 6 in combination with a pharmaceutically acceptable diluent or carrier.

10. A method of treating acute or chronic inflammatory or autoimmune diseases mediated by LFA-1/ICAM-1, -ICAM-2 or -ICAM-3 interactions which comprises administering systemically or topically to a subject in need of such treatment an effective amount of a compound according to claim 1.

11. A method of treating inflammatory and hyperproliferative skin diseases mediated by LFA-1/ICAM-1, -ICAM-2 or -ICAM-3 interactions which comprises administering systemically or topically to a subject in need of such treatment an effective amount of a compound according to claim 1.

12. A method according to claim 11 of treating psoriasis and atopic dermatitis.

13. A method according to claim 11 of treating allergic contact dermatitis.

14. A method of treating acute or chronic inflammatory or autoimmune diseases mediated by LFA-1/ICAM-1, -ICAM-2- or -ICAM-3 interactions which comprises administering systemically or topically to a subject in need of such treatment an effective amount of a compound according to claim 6.

15. A method of treating inflammatory and hyperproliferative skin diseases mediated by LFA-1/ICAM-1, -ICAM-2 or -ICAM-3 interactions which comprises administering systemically or topically to a subject in need of such treatment an effective amount of a compound according to claim 6.

16. A method according to claim 15 of treating psoriasis and atopic dermatitis.

17. A method according to claim 15 of treating allergic contact dermatitis.

* * * * *

UNITED STATES PATENT AND TRADEMARK OFFICE
CERTIFICATE OF CORRECTION

PATENT NO.   : 6,399,599 B1
DATED        : June 4, 2002
INVENTOR(S)  : Rainer Albert et al.

It is certified that error appears in the above-identified patent and that said Letters Patent is hereby corrected as shown below:

<u>Column 14,</u>
Line 42, should read:
-- X is —CN, —NR$_5$R$_6$, or —O—R$_8$ wherein R$_5$ is H, --.

<u>Column 15,</u>
Line 37, the omitted structural formula should read:
-- X$_1$—CO—Y'''—X$_2$    IIIc --.

Signed and Sealed this

Twenty-sixth Day of November, 2002

Attest:

Attesting Officer

JAMES E. ROGAN
*Director of the United States Patent and Trademark Office*